US011111210B2

(12) United States Patent
Wainer

(10) Patent No.: US 11,111,210 B2
(45) Date of Patent: Sep. 7, 2021

(54) PHENYL CYCLOHEXANONE DERIVATIVES AND METHODS OF MAKING AND USING THEM

(71) Applicant: SPIRIFY PHARMA INC, Saddle Brook, NJ (US)

(72) Inventor: Irving W. Wainer, Washington, DC (US)

(73) Assignee: SPIRIFY PHARMA INC., Saddle Brook, NJ (US)

( * ) Notice: Subject to any disclaimer, the term of this patent is extended or adjusted under 35 U.S.C. 154(b) by 672 days.

(21) Appl. No.: 15/777,374

(22) PCT Filed: Nov. 15, 2016

(86) PCT No.: PCT/US2016/062039
§ 371 (c)(1),
(2) Date: May 18, 2018

(87) PCT Pub. No.: WO2017/087388
PCT Pub. Date: May 26, 2017

(65) Prior Publication Data
US 2021/0002214 A1 Jan. 7, 2021

Related U.S. Application Data

(60) Provisional application No. 62/256,900, filed on Nov. 18, 2015.

(51) Int. Cl.
| | | |
|---|---|---|
| C07C 311/14 | (2006.01) |
| C07C 225/28 | (2006.01) |
| C07C 255/46 | (2006.01) |
| C07D 207/09 | (2006.01) |
| C07D 233/24 | (2006.01) |
| C07D 307/14 | (2006.01) |

(52) U.S. Cl.
CPC .......... *C07C 311/14* (2013.01); *C07C 225/28* (2013.01); *C07C 255/46* (2013.01); *C07D 207/09* (2013.01); *C07D 233/24* (2013.01); *C07D 307/14* (2013.01)

(58) Field of Classification Search
None
See application file for complete search history.

(56) References Cited

U.S. PATENT DOCUMENTS

| | | | |
|---|---|---|---|
| 9,650,352 B2 * | 5/2017 | Wainer | A61P 21/02 |
| 2004/0248964 A1 | 12/2004 | Crooks et al. | |
| 2014/0296241 A1 | 10/2014 | Wainer et al. | |
| 2015/0259277 A1 | 9/2015 | Sleigh et al. | |

FOREIGN PATENT DOCUMENTS

| | | |
|---|---|---|
| EP | 0194984 A1 | 9/1986 |
| WO | 2013056229 A1 | 4/2013 |

OTHER PUBLICATIONS

Rantamaki et al. "Antidepressant drug action—From rapid changes on network function to network rewiring" Progress in Neuro-Psychopharmacology & Biological Psychiatry, 2016, vol. 64, pp. 285-292, available online Jun. 9, 2015.*
International Search Report and Written Opinion issued in PCT/US16/62039 dated Feb. 1, 2017.

* cited by examiner

*Primary Examiner* — Joseph R Kosack
(74) *Attorney, Agent, or Firm* — The Roy Gross Law Firm, LLC; Roy Gross

(57) ABSTRACT

Phenyl cyclohexanone based active agents, pharmaceutical preparations containing such active agents, methods of modifying cellular activity by contacting cells with such active agents, and methods of treating various conditions by administering such active agents to a patient are described.

20 Claims, No Drawings

PHENYL CYCLOHEXANONE DERIVATIVES AND METHODS OF MAKING AND USING THEM

CROSS REFERENCE TO RELATED APPLICATION

This application is a national stage of International Application No. PCT/US2016/062039 filed Nov. 15, 2016, which claims priority to and the benefit of U.S. Provisional Application Ser. No. 62/256,900 filed on Nov. 18, 2015, the entire contents of which are incorporated herein by reference.

BACKGROUND

Drugs useful for the treatment of bipolar depression, major depressive disorder, neuropathic pain, and chronic pain, including complex regional pain syndrome (CRPS) are desirable. Frequently, however, drugs useful for the treatment of these conditions may be hindered by unwanted central nervous system (CNS) effects, may result in serious side effects, and/or may present a significant potential for abuse.

A need exists for therapeutics exhibiting the aforementioned, desirable therapeutic properties without CNS effects, serious side effects, or the potential for abuse.

SUMMARY

This disclosure relates to active agents, pharmaceutical preparations containing such agents, and methods of treating various conditions by administering such active agents. The active agents are derivatives of phenyl cyclohexanones.

In a first aspect, the present disclosure provides a compound of Formula I or a pharmaceutically acceptable salt thereof:

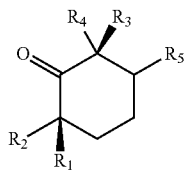

Within Formula I the variables, e.g. $R_1$-$R_5$, carry the definitions set forth below:

$R_1$ is —$NH_2$ or —OH;

$R_2$ is

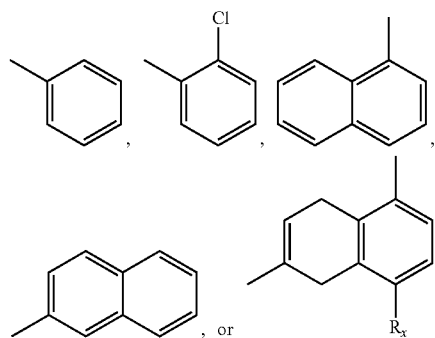

where $R_x$ is Cl, Br, —$OCH_3$, or —$NH_2$;

$R_3$ is —OH, —$OCH_3$, —$NH_2$, —CN, —$SO_2$—$NH_2$,

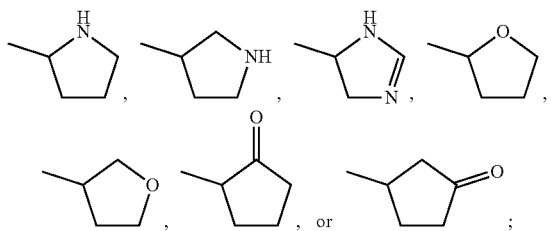

$R_4$ is —H, —OH, or —$OCH_3$; and $R_5$ is —OH, —$NH_2$, or =O.

In another aspect, the present disclosure provides a pharmaceutical composition including a compound of Formula I or a pharmaceutically acceptable salt thereof, together with a pharmaceutically acceptable excipient.

In another aspect, the present disclosure provides a method of treating a patient in need of treatment by administering a pharmaceutical composition containing a therapeutically effective amount of a compound of Formula I or a pharmaceutically acceptable salt thereof, together with a pharmaceutically acceptable carrier. In embodiments, the patient is in need of treatment for bipolar depression, major depressive disorder, schizophrenia, Alzheimer's dementia, amyotrophic lateral sclerosis, complex regional pain syndrome (CRPS), chronic pain, or neuropathic pain.

DETAILED DESCRIPTION

Terminology

Compounds disclosed herein are described using standard nomenclature. Unless defined otherwise, all technical and scientific terms used herein have the same meaning as is commonly understood by one of skill in the art to which this disclosure pertains.

The terms "a" and "an" do not denote a limitation of quantity, but rather denote the presence of at least one of the referenced item.

Formula I includes all subformulae thereof. For example Formula I includes compounds of Formula I and Formula II-XVI and the pharmaceutically acceptable salts, prodrugs and other derivatives, hydrates, polymorphs, and thereof.

The term "chiral" refers to molecules having the property of non-superimposability of the mirror image partner.

"Stereoisomers" are compounds having identical chemical constitution, but differ with regard to the arrangement of the atoms or groups in space.

A "Diastereomer" is a stereoisomer with two or more centers of chirality and whose molecules are not mirror images of one another. Diastereomers have different physical properties, e.g., melting points, boiling points, spectral properties, and reactivities. Mixtures of diastereomers may separate under high resolution analytical procedures such as electrophoresis, crystallization in the presence of a resolving agent, or chromatography, using, for example, a chiral HPLC column.

"Enantiomers" refer to two stereoisomers of a compound which are non-superimposable mirror images of one another. A 50:50 mixture of enantiomers is referred to as a racemic mixture or a racemate, which may occur where there has been no stereoselection or stereospecificity in a chemical reaction or process.

Stereochemical definitions and conventions used herein generally follow S. P. Parker, Ed., McGraw-Hill *Dictionary* of Chemical Terms (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory.

A "racemic mixture" or "racemate" is an equimolar (or 50:50) mixture of two enantiomeric species, devoid of optical activity. A racemic mixture may occur where there has been no stereoselection or stereospecificity in a chemical reaction or process.

Where a compound exists in various tautomeric forms, the disclosure is not limited to any one of the specific tautomers, but rather includes all tautomeric forms.

The disclosure includes compounds of Formula I having all possible isotopes of atoms occurring in the compounds. Isotopes include those atoms having the same atomic number but different mass numbers. By way of general example, and without limitation, isotopes of hydrogen include tritium and deuterium and isotopes of carbon include $^{11}C$, $^{13}C$, and $^{14}C$.

Certain compounds are described herein using a general formula that includes variables, e.g. $R_1$-$R_4$. Unless otherwise specified, each variable within Formula I is defined independently of other variables. Thus, if a group is said to be substituted, e.g. with 0-2 $R^*$, then said group may be substituted with up to two $R^*$ groups and $R^*$ at each occurrence is selected independently from the definition of $R^*$. Also, combinations of substituents and/or variables are permissible only if such combinations result in stable compounds.

The term "substituted" as used herein means that at least one hydrogen on the designated atom or group is replaced with a selection from the indicated group, provided that the designated atom's normal valence is not exceeded. When the substituent is oxo (i.e., =O), then 2 hydrogens on the atom are replaced. When aromatic moieties are substituted by an oxo group, the aromatic ring is replaced by the corresponding partially unsaturated ring. For example a pyridyl group substituted by oxo is a pyridone. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation into an effective therapeutic agent.

A dash ("-") that is not between two letters or symbols is used to indicate a point of attachment for a substituent. For example, —$(CH_2)C_3$-$C_7$ cycloalkyl is attached through carbon of the methylene ($CH_2$) group.

The term "heterocycle" indicates a 5- to 8-membered saturated, partially unsaturated, or aromatic ring containing from 1 to about 4 heteroatoms chosen from N, O, and S, with remaining ring atoms being carbon, or a 7 to 11 membered bicyclic saturated, partially unsaturated, or aromatic heterocyclic ring system or a 10 to 15-membered tricyclic ring system, containing at least 1 heteroatom in the multiple ring system chosen from N, O, and S and containing up to about 4 heteroatoms independently chosen from N, O, and S in each ring of the multiple ring system. Unless otherwise indicated, the heterocyclic ring may be attached to the group it substitutes at any heteroatom or carbon atom that results in a stable structure. When indicated the heterocyclic rings described herein may be substituted on carbon or on a nitrogen atom if the resulting compound is stable. A nitrogen atom in the heterocycle may optionally be quaternized. In embodiments, the total number of heteroatoms in a heterocyclic groups is not more than 4 and that the total number of S and O atoms in a heterocyclic group is not more than 2, more preferably not more than 1. Examples of heterocyclic groups include, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, dihydroisoindolyl, 5,6,7,8-tetrahydroisoquinoline, pyridinyl, pyrimidinyl, furanyl, thienyl, pyrrolyl, pyrazolyl, pyrrolidinyl, morpholinyl, piperazinyl, piperidinyl, and pyrrolidinyl.

"5- or 6-membered heteroaryl" indicates a stable 5- to 6-membered monocyclic ring that contains from 1 to 4, or preferably from 1 to 3, heteroatoms chosen from N, O, and S, with remaining ring atoms being carbon. When the total number of S and O atoms in the heteroaryl group exceeds 1, these heteroatoms are not adjacent to one another. In embodiments, the total number of S and O atoms in the heteroaryl group is not more than 2. In other embodiments, the total number of S and O atoms in the heteroaryl group is not more than 1. A nitrogen atom in a heteroaryl group may optionally be quaternized. When indicated, such heteroaryl groups may be further substituted with carbon or non-carbon atoms or groups. Such substitution may include fusion to a 5 to 7-membered saturated cyclic group that optionally contains 1 or 2 heteroatoms independently chosen from N, O, and S, to form, for example, a [1,3]dioxolo[4,5-c]pyridyl group. Examples of heteroaryl groups include, but are not limited to, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, and 5,6,7,8-tetrahydroisoquinoline.

"Heterocycloalkyl" means a saturated cyclic group containing from 1 to about 3 heteroatoms chosen from N, O, and S, with remaining ring atoms being carbon. Heterocycloalkyl groups have from 3 to about 8 ring atoms, and more typically have from 5 to 7 ring atoms. Examples of heterocycloalkyl groups include morpholinyl, piperazinyl, piperidinyl, and pyrrolidinyl groups. A nitrogen in a heterocycloalkyl group may optionally be quaternized.

"Haloalkyl" indicates both branched and straight-chain alkyl groups having the specified number of carbon atoms, substituted with one or more halogen atoms, generally up to the maximum allowable number of halogen atoms. Examples of haloalkyl include, but are not limited to, trifluoromethyl, difluoromethyl, 2-fluoroethyl, and pentafluoroethyl.

"Haloalkoxy" indicates a haloalkyl group as defined above attached through an oxygen bridge (oxygen of an alcohol radical).

"Halo" or "halogen" as used herein refers to fluoro, chloro, bromo, or iodo.

An "active agent" means any compound, element, or mixture that when administered to a patient alone or in combination with another agent confers, directly or indirectly, a physiological effect on the patient. When the active agent is a compound, salts, solvates (including hydrates) of the free compound or salt, crystalline and non-crystalline forms, as well as various polymorphs of the compound are included. Compounds may contain one or more asymmetric elements such as stereogenic centers, stereogenic axes and the like, e.g. asymmetric carbon atoms, so that the compounds can exist in different stereoisomeric forms. These compounds can be, for example, racemates or optically active forms.

"Administration" means dispensing a compound or composition containing the compound for use via any appropriate route, for example, oral administration, in either solid or liquid dosage form, inhalation, injection, suppository administration, or transdermal contact. "Administration" also includes applying a compound or composition containing the compound via any appropriate route such as via oral administration, in either solid or liquid dosage form, inhalation, injection, suppository administration, or transdermal contact.

"Depressive symptoms" include low mood, diminished interest in activities, psychomotor slowing or agitation, changes in appetite, poor concentration or indecisiveness, excessive guilt or feelings of worthlessness, and suicidal ideations. Depressive symptoms may occur in the context of depressive disorders, bipolar disorders, mood disorders due to a general medical condition, substance-induced mood disorders, other unspecified mood disorders, and also may be present in association with a range of other psychiatric disorders, including but not limited to psychotic disorders, cognitive disorders, eating disorders, anxiety disorders and personality disorders. The longitudinal course of the disorder, the history, and type of symptoms, and etiologic factors help distinguish the various forms of mood disorders from each other.

"Depression symptoms rating scale" refers to any one of a number of standardized questionnaires, clinical instruments, or symptom inventories utilized to measure symptoms and symptom severity in depression. Such rating scales are often used in clinical studies to define treatment outcomes, based on changes from the study's entry point(s) to endpoint(s). Such depression symptoms rating scales include, but are not limited to, The Quick Inventory of Depressive-Symptomatology Self-Report (QIDS-$SR_{16}$), the 17-Item Hamilton Rating Scale of Depression ($HRSD_{17}$), the 30-Item Inventory of Depressive Symptomatology (IDS-$C_{30}$), or The Montgomery-Asperg Depression Rating Scale (MADRS). Such ratings scales may involve patient self-report or may be clinician rated. A 50% or greater reduction in a depression ratings scale score over the course of a clinical trial (starting point to endpoint) is typically considered a favorable response for most depression symptoms rating scales. "Remission" in clinical studies of depression often refers to achieving at, or below, a particular numerical rating score on a depression symptoms rating scale (for instance, less than or equal to 7 on the $HRSD_{17}$; or less than or equal to 5 on the QIDS-$SR_{16}$; or less than or equal to 10 on the MADRS).

A "patient" means any human or non-human animal in need of medical treatment. Medical treatment can include treatment of an existing condition, such as a disease or disorder, prophylactic or preventative treatment, or diagnostic treatment. In some embodiments the patient is a human patient.

"Pharmaceutical compositions" are compositions comprising at least one active agent, such as a compound or salt of Formula I, and at least one other substance, such as a carrier, excipient, or diluent.

The term "carrier" applied to pharmaceutical compositions of in accordance with the disclosure refers to a diluent, excipient, or vehicle with which an active compound is administered.

A "pharmaceutically acceptable excipient" means an excipient that is useful in preparing a pharmaceutical composition that is generally safe, non-toxic, and neither biologically nor otherwise undesirable, and includes an excipient that is acceptable for veterinary use as well as human pharmaceutical use. A "pharmaceutically acceptable excipient" as used herein includes both one and more than one such excipient.

"Pharmaceutically acceptable salts" are derivatives of the disclosed compounds, wherein the parent compound is modified by making non-toxic acid or base addition salts thereof, and further refers to pharmaceutically acceptable solvates, including hydrates, of such compounds and such salts. Examples of pharmaceutically acceptable salts include, but are not limited to, mineral or organic acid addition salts of basic residues such as amines; alkali or organic addition salts of acidic residues such as carboxylic acids; and the like, and combinations comprising one or more of the foregoing salts. The pharmaceutically acceptable salts include non-toxic salts and the quaternary ammonium salts of the parent compound formed, for example, from non-toxic inorganic or organic acids. For example, non-toxic acid salts include those derived from inorganic acids such as hydrochloric, hydrobromic, sulfuric, sulfamic, phosphoric, nitric and the like; other acceptable inorganic salts include metal salts such as sodium salt, potassium salt, cesium salt, and the like; and alkaline earth metal salts, such as calcium salt, magnesium salt, and the like, and combinations comprising one or more of the foregoing salts.

Pharmaceutically acceptable organic salts include salts prepared from organic acids such as acetic, trifluoroacetic, propionic, succinic, glycolic, stearic, lactic, malic, tartaric, citric, ascorbic, pamoic, maleic, hydroxymaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like; organic amine salts such as triethylamine salt, pyridine salt, picoline salt, ethanolamine salt, triethanolamine salt, dicyclohexylamine salt, N,N'-dibenzylethylenediamine salt, and the like; and amino acid salts such as arginate, asparginate, glutamate, and the like, and combinations comprising one or more of the foregoing salts.

The term "therapeutically effective amount" or "effective amount" means an amount effective, when administered to a human or non-human patient, to provide any therapeutic benefit. A therapeutic benefit may be an amelioration of symptoms, e.g., an amount effective to decrease the symptoms of a depressive disorder or pain. A therapeutically effective amount of a compound is also an amount sufficient to provide a significant positive effect on any indicia of a disease, disorder, or condition e.g. an amount sufficient to significantly reduce the frequency and severity of depressive symptoms or pain. A significant effect on an indicia of a disorder or condition includes a statistically significant in a standard parametric test of statistical significance such as Student's T-test, where $p<0.05$; though the effect need not be significant in some embodiments.

Chemical Description of Compound Structure and Compound Embodiments

Active agents in accordance with the present disclosure are compounds of the following Formula I or pharmaceutically acceptable salts thereof:

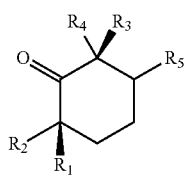

Within Formula I the variables, e.g. $R_1$-$R_5$, carry the definitions set forth below:

$R_1$ is —$NH_2$ or —OH;

$R_2$ is

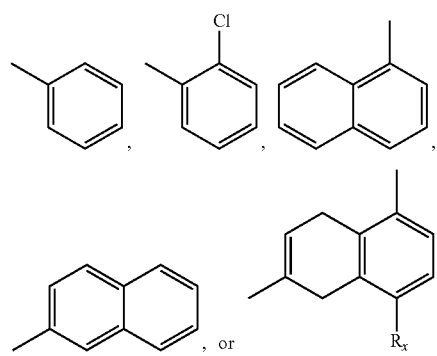

where $R_x$ is Cl, Br, —$OCH_3$, or —$NH_2$;

$R_3$ is —OH, —$OCH_3$, —$NH_2$, —CN, —$SO_2$—$NH_2$,

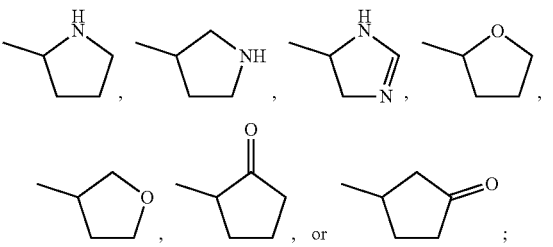

$R_4$ is —H, —OH, or —$OCH_3$; and $R_5$ is —OH, —$NH_2$, or =O.

The disclosure includes all stereoisomers of compounds of Formula I.

Illustrative examples of active agents in accordance with the present disclosure include the following compounds:

Formula II

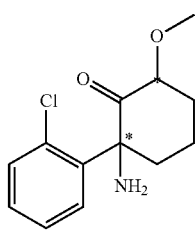

Formula III

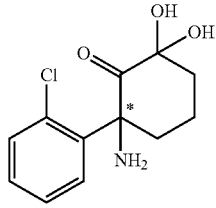

Formula IV

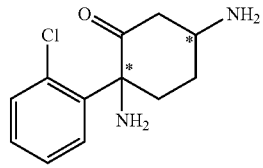

Formula V

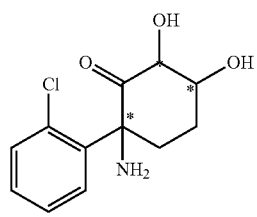

Formula VI

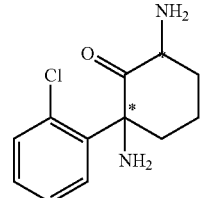

Formula VII

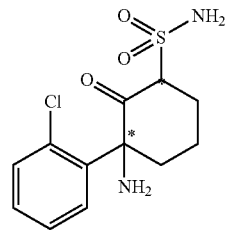

Formula VIII

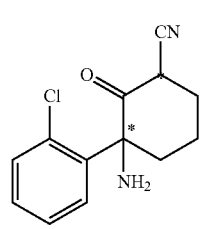

Formula IX

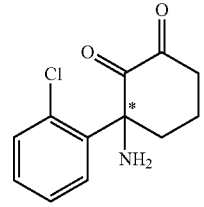

Formula X

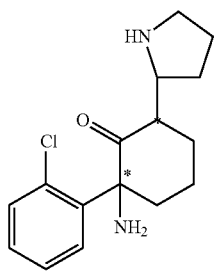

Formula XI

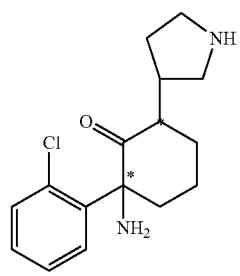

Formula XII

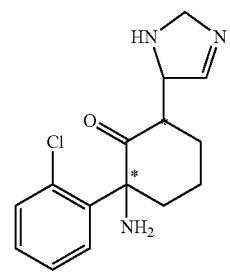

Formula XIII

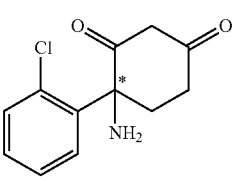

Formula XIV

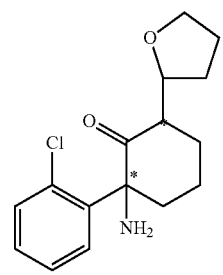

Formula XV

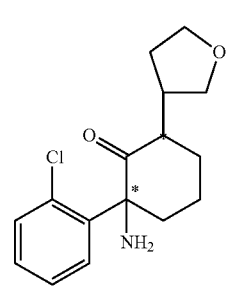

Formula XVI

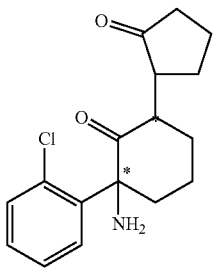

Methods of Making the Present Compounds

Those skilled in the art of organic chemistry reading this disclosure will readily envision methods of synthesizing compounds in accordance with the present disclosure. For example, using 2-amino-6-bromocyclohexanone (the synthesis of which is described in WO2013/056229) as a starting material, well known reaction mechanisms may be employed to replace bromine with a desired substituent to arrive at compounds in accordance with the present disclosure.

To prepare (+,−)-(Z+E)-2-amino-6-bromocyclohexanone, which may be used as a starting material in synthesizing compounds in accordance with the present disclosure, racemic (+,−)-2-amino-2-(2-chlorophenyl)cyclohexan-1-one (free base) (10.0 g, 35.8 mmol) in 50 mL glacial acetic acid is treated with pyridinium tribromide (16.4 g, 51.3 mmol). The resulting mixture is heated at 130° C. for one hour using microwaves. The solvent is removed in vacuo and the crude material is dissolved in $CHCl_3$ and washed with saturated $NaHCO_3$, dried ($Na_2SO_4$) and evaporated in vacuo leaving 12.4 g of a crude product mixture of diasteriomers (Z+E, 3:1). This crude product mixture of diasteriomers may be chromatographed using silica gel, eluting with a varying concentration of $CH_2Cl_2$/MeOH/$Et_3$N from (99.9/0/0.1) to (98.9/1/0.1) to give pure separated isomers.

To prepare the compound of Formula II, (+,−)-(Z)-2-amino-6-bromocyclohexanone may be subjected to a Williamson Ether Synthesis where a deprotonated alcohol ("alkoxide") replaces bromide in 2-amino-6-bromocyclohexanone to form an ether, typically in a the presence of a base (such as sodium or potassium hydride) in a polar aprotic solvent (such as acetonitrile or DMSO).

Synthesis of (+,−)-(2S,6R/2R,6S)-2-amino-6-aminocyclohexanone (Formula VI)

Racemic (+,−)-(Z)-2-amino-6-bromocyclohexanone in dry THF is heated under reflux with $NaNH_3$ for 24 hours. The resulting solution is acidified and extracted with water. The water extracts are made basic and extracted with diethylether. The diethylether extracts, are combined, dried and evaporated to dryness. The crude product mixture is dissolved in DMSO (10 mL) and purified by injections onto a preparative HPLC. Gradient HPLC: Waters Sunfire Prep C18 (10 micron), 150×30 mm; 5 mM Ammonium Formate in Water/Acetonitrile (90/10) for 5 minutes then (90/10) to (10/90) over 10 minutes then hold; 10 mL/min, 270 nm; $R_t$ 9.5 minutes. Product fractions are combined and evaporated in vacuo giving (+,−)-(2S,6R/2R,6S)-2-amino-6-cyanocyclohexanone.

Synthesis of (+,−)-(2S,6R/2R,6S)-2-amino-6-cyanocyclohexanone (Formula VIII)

A sample of racemic (+,−)-(Z)-2-amino-6-bromocyclohexanone in dry THF is heated with NaCN under reflux for 24 hours The resulting solution is acidified and extracted with water. The water extracts are made basic and extracted with diethylether. The diethylether extracts, are combined, dried and evaporated to dryness. The crude product mixture is dissolved in DMSO (10 mL) and purified by injections onto a preparative HPLC. Gradient HPLC: Waters Sunfire Prep C18 (10 micron), 150×30 mm; 5 mM Ammonium Formate in Water/Acetonitrile (90/10) for 5 minutes then (90/10) to (10/90) over 10 minutes then hold; 10 mL/min, 270 nm; $R_t$ 9.5 minutes. Product fractions are combined and evaporated in vacuo giving (+,−)-(2S,6R/2R,6S)-2-amino-6-cyanocyclohexanone.

Synthesis of (+,−)-(2S,6R/2R,6S)-2-amino-6-imidazolecyclohexanone (Formula XII)

A compound of Formula XII may be prepared in a method analogous to the method for producing imidazole derivatives disclosed in EP 0194984 A1. In an illustrative synthesis, the imidazole is reacted with benzloxymethylpyrrole or other appropriate protecting agent and then treated with butyllithium in anhydrous THF. The solution is cooled and a sample of racemic (+,−)-(Z)-2-amino-6-bromocyclohexanone in dry THF is slowly added under an argon atmosphere with constant stirring. The resulting solution is allowed to reach room temperature and the stirring continued for 24 h. The resulting solution is acidified and extracted with water. The water extracts are made basic and extracted with diethylether. The diethylether extracts, are combined, dried and evaporated to dryness. The crude product mixture is dissolved in DMSO (10 mL) and purified by injections onto a preparative HPLC. Gradient HPLC: Waters Sunfire Prep C18 (10 micron), 150×30 mm; 5 mM Ammonium Formate in Water/Acetonitrile (90/10) for 5 min then (90/10) to (10/90) over 10 min then hold; 10 mL/min, 270 nm; Rt 9.5 min. Product fractions are combined and evaporated in vacuo giving (+,−)-(2S,6R/2R,6S)-2-amino-6-imadazolecyclohexanone.

Those skilled in the art reading this disclosure will readily envision methods of synthesizing other compounds in accordance with the present disclosure.

Compound Function

Since D-Serine concentrations have been correlated with a number of CNS diseases such as amyotrophic lateral sclerosis (ALS), Alzheimer's and schizophrenia, the development of drugs that can modulate D-serine expression and distribution is an area of pharmacological and clinical interest. Without wishing to be bound to any particular theory, it is believed that certain compounds of Formula I exert activity via modification of endogenous concentrations of D-serine. Reduction in the concentration of D-serine may produce an "indirect" inhibition of the N-methyl-D-aspartate (NMDA) receptor. D-Serine is an endogenous NMDA receptor co-agonist that plays a critical role in long-term potentiation and NMDA-induced neurotoxicity. Reduced D-serine concentration is associated with reduced NMDA receptor activity. Certain compounds of Formula I may inhibit NMDA (N-methyl-D-aspartic acid) receptors by inhibiting serine racemase (SR) and thereby limiting the concentration of D-serine available to interact with the NMDA receptor. As a result, the presently described active agents may be of use in the treatment of depression, Alzheimer's disease, ALS, Parkinson's disease and schizophrenia by inhibiting the NMDA receptor.

Certain compounds of Formula I may also be serine racemase (SR) inhibitors. Thus, the present disclosure also provides a method of inhibiting SR by contacting cells with a concentration of a compound of Formula I sufficient to inhibit SR.

Certain compounds of Formula I may also stimulate the activating phosphorylation of the mammalian target of rapamycin (mTOR) and its downstream targets. This activity may also be associated with antidepressant effects of the presently described compounds.

Certain compounds of Formula I may also exhibit inhibitory activity with respect to nicotinic acetylcholine receptors (nAChR) such as, for example, nAChR subtypes, $\alpha_7$ and $\alpha_3\beta_4$ nAChR, known to be targets in analgesia. An indirect inhibition of SR activity by the present compounds or their metabolites through the inhibition of nAChR activity may also occur.

Compounds of Formula I may transform into an array of hydroxylated metabolites which may be associated with antidepressant effects exhibited by the presently described compounds.

Structural, steric and stereochemical factors may contribute to the modulation of intracellular D-serine concentration and SR expression. For example, the potency of the compounds $IC_{50}$ values associated with a decrease in intracellular D-serine may be affected by the molecular structure of the compounds. In some cases, increased potency of the compound, reflected as a decrease in $IC_{50}$ values will be the result of enhanced hydrogen bond donating-accepting properties of a substituent at the C6 position on the cyclohexanone ring of the compounds according to Formula I.

In some compounds, the stereochemical relationship between the two chiral centers may play a role in the relative potency of the compounds as measured by the calculated $IC_{50}$ values. A cis stereochemical relationship between the C2 and C6 chiral centers on the cyclohexanone ring may be more potent with lower $IC_{50}$ values relative to compounds with a trans relationship between the two chiral centers.

With certain compounds, the cyclohexanone ring is in a favorable steric environment when the C2 carbon is in an S configuration. In embodiments, the cis orientation and a 5-configuration at C2 may result in lower $IC_{50}$ values. Furthermore, an additional stabilizing interaction, most probably hydrogen bonding, may occur between the present compounds and the target receptor.

Determination of Endogenous Concentrations of D-Serine

The following materials and methods may be used to determine the effect of the present compositions on endogenous concentrations of D-serine.

Maintenance And Treatment Of Cell Lines

The PC-12 cell line, which is derived from rat adrenal medulla, may be obtained from American Type Culture Collection (Manassas, Va., USA). The PC-12 cells are maintained in RPMI-1640 (Quality Biological, Gaithersburg, Md., USA) supplemented with 4-(2-hydroxyethyl)-1-piperazineethanesulfonic acid (HEPES) buffer [1 mM, pH 7.4] (Mediatech, Inc., Manassas, Va., USA), 10% heat-inactivated horse serum (Biosource, Rockville, Md., USA), 5% fetal bovine serum (FBS), 1% sodium pyruvate, 5% L-glutamine and 1% penicillin/streptomycin (which may all be purchased from (Quality Biological).

Incubation of PC-12 Cells With Test Compounds

Cells are seeded on 100×20 mm tissue culture plates and maintained at 37° C. under humidified 5% $CO_2$ in air until they reach >70% confluence. The original media is replaced with media containing the test compounds and the plates are incubated for an additional 36 h, unless otherwise indicated. The medium is removed, and the cells collected for analysis. The cells are assessed for intracellular and extracellular D-serine levels, and expression of monomeric and dimeric forms of serine racemase (SR). The intracellular D-serine levels are determined in triplicate dishes while the determination of SR protein expression is carried out on one set of dishes. Additionally, extracellular D-serine levels are determined in cells treated with the test compounds. All analyses may be repeated in three independent cell cultures (n=3).

Determination Of Intracellular and Extracellular D-Ser Concentrations

Intracellular D-serine concentrations are measured using a previously described and validated capillary electrophoresis-laser induced fluorescence (CE-LIF) method using a P/ACE MDQ system equipped with a laser-induced fluorescence detector (Beckman Instruments, Fullerton, Calif., USA). See, Singh et al., Anal Biochem 2012; 421: 460-466. The extracellular D-serine levels are determined using a previously reported assay employing liquid chromatography with mass spectrometric detection. See, Singh et al., Br J Pharmacol 2015; 172: 4546-59.

Measurement of Monomeric-SR (m-SR) and Dimeric-SR (d-SR)

Expression by Western Blotting

The expression of m-SR and d-SR in PC-12 cells may be determined using a previously described procedure. See, Singh et al., Anesthesiology 2014; 121:149-59. The primary antibody for d-SR may be obtained from Santa Cruz Biotechnology (Dallas, Tex., USA), and the antibody that recognizes both m-SR and d-SR may be purchased from Abcam, Inc. (Cambridge, Mass.). The primary antibody for β-actin is from Abcam. The antibodies are used at a dilution recommended by the manufacturer. Imunoreactive bands may be detected using the ECL Plus Western Blotting Detection System (GE Healthcare, Piscataway, N.J., USA) and quantification may be accomplished by volume densitometry using ImageJ software (National Institutes of Health, Bethesda, Md.) and normalization to β-actin.

Comparative Molecular Field Analysis (CoMFA)

The CoMFA model may be generated using methodology implemented in Sybyl-X 2.1.1 (Certara, L.P.). The molecular models of structures may be prepared in HyperChem v. 6.03 (HyperCube Inc., Gainesville, Fla.) using Model Build procedure to ensure the same conformation of the common scaffold. The models are extracted to Sybyl and the Gasteiger-Huckel atomic charges are calculated. The models are aligned using 2-chlorobenzyl moiety as a common substructure. Two types of molecular fields (steric and electrostatic) are sampled on the grid lattice surrounding each structure. In the procedure default settings are used. The $pIC_{50}$ values presenting effects on the intracellular D-serine levels in PC-12 cells of the test compounds are subjected to 3D-QSAR modeling.

Statistical Analysis

Prism 4 (GraphPad Software, Inc., La Jolla, Calif., USA) running on a personal computer may be used to perform all statistical data analysis, including $IC_{50}$ value calculations. The effect of test compounds on intracellular D-serine concentration may be reported as 'average percent change±standard deviation' compared to control values. Differences between two groups may be analyzed using Student's t-test (unpaired, two-tailed). A P value $\leq 0.05$ is considered significant.

Pharmaceutical Compositions

Compounds disclosed herein can be administered as the neat chemical, but in embodiments are administered as a pharmaceutical composition. Accordingly, the disclosure provides pharmaceutical compositions including a compound or pharmaceutically acceptable salt of Formula I, together with at least one pharmaceutically acceptable carrier. The pharmaceutical composition may contain a compound or salt of Formula I as the only active agent, but in embodiments the composition contains at least one additional active agent. In certain embodiments the pharmaceutical composition is an oral dosage form that contains from about 0.1 mg to about 1000 mg, from about 1 mg to about 500 mg, or from about 10 mg to about 200 mg of a compound of Formula I and optionally from about 0.1 mg to about 2000 mg, from about 10 mg to about 1000 mg, from about 100 mg to about 800 mg, or from about 200 mg to about 600 mg of an additional active agent in a unit dosage form.

Compounds disclosed herein may be administered orally, topically, parenterally, by inhalation or spray, sublingually, transdermally, via buccal administration, rectally, as an ophthalmic solution, or by other means, in dosage unit formulations containing conventional pharmaceutically acceptable carriers. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose. The dosage form may provide immediate release, sustained release, or a combination thereof. Gastro-retentive dosage forms are also contemplated.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the active agents in accordance with this disclosure.

The pharmaceutical compositions can be formulated for oral administration. Preferred oral dosage forms are formulated for once a day or twice a day administration. These compositions contain between 0.1 and 99 weight % (wt. %) of a compound of Formula I and usually at least about 5 wt. % of a compound of Formula I. Some embodiments contain from about 25 wt. % to about 50 wt. % or from about 5 wt. % to about 75 wt. % of the compound of Formula I.

Methods of Treatment

Methods of treatment in accordance with the present disclosure include administering a compound of Formula I or any combination of compounds of Formula I. Methods of treatment also include administering a compound of Formula I in optically pure form.

Methods of treatment in accordance with the present disclosure include methods of treating bipolar depression, major depressive disorder, schizophrenia, Alzheimer's dementia, amyotrophic lateral sclerosis, complex regional pain syndrome (CRPS), chronic pain, or neuropathic pain by administering a pharmaceutical composition containing an effective amount of a compound of Formula I or a pharmaceutically acceptable salt thereof, together with a pharmaceutically acceptable carrier to a patient in need of such treatment.

Methods of treatment include providing certain dosage amounts of a compound or pharmaceutically acceptable salt of Formula I to a patient. Dosage levels of each active agent of from about 0.1 mg to about 140 mg per kilogram of body weight per day are useful in the treatment of the above-indicated conditions (about 0.5 mg to about 7 g per patient per day). The amount of active ingredient that may be combined with the carrier materials to produce a single unit dosage form will vary depending upon the patient treated and the particular mode of administration.

In certain embodiments, a therapeutically effect amount is an amount that provides a plasma $C_{max}$ of a compound of Formula I of about of 0.25 mcg/mL to about 125 mcg/mL, or about 1 mcg/mL to about 50 mcg/mL. For peripheral indications, formulations and methods that provide a $C_{max}$ of about 0.25 mcg/mL to about 25 mcg/mL may be employed, while for CNS indications, formulations and methods that provide a plasma $C_{max}$ of about 0.25 mcg/mL to about 125 mcg/mL may be employed. The disclosure also includes IV pharmaceutical compositions that provide about 0.2 mg to about 500 mg per dose of a compound of Formula I, for peripheral indications, compounds that provide about 0.5 mg to about 500 mg/dose may be employed.

The compound or salt of Formula I may be the only active agent administered or may be administered together with an additional active agent. For example, the compound of Formula I may administered together with another active agent chosen from any of the following non-limiting examples:

Antidepressants, such as, for example, escitalopram, fluoxetine, paroxetine, duloxetine, sertraline, citalopram, bupropion, venlafaxine, duloxetine, naltrexone, mirtazapine, venlafaxine, atomoxetine, bupropion, doxepin, amitriptyline, clomipramine, nortriptyline, buspirone, aripiprazole, clozapine, loxapine, olanzapine, quetiapine, risperidone, ziprasidone, carbamazepine, gabapentin, lamotrigine, phenyloin, pregabalin, donepezil, galantamine, memantine, rivastigmine, tramiprosate, or pharmaceutically active salts or prodrugs thereof, or a combination of the foregoing;

Schizophrenia Medications, such as, for example, aripiprazole, lurasidone, asenapine, clozapine, ziprasidone, risperidone, quetiapine, stelazine, olanzapine, loxapine, flupentioxol, perphenazine, haloperidol, chlorpromazine, fluphenazine, prolixin, or paliperidone;

Alzheimer's Dementia Medications, such as, for example, donepezil, rivastigmine, galantamine, or memantine;

ALS Medications, such as, for example, riluzole;

Pain Medications, such as, for example, acetaminophen, aspirin, NSAIDS, including Diclofenac, Diflunisal, Etodolac, Fenoprofen, Flurbiprofen, Ibuprofen, Indomethacin, Ketoprofen, Ketorolac, Meclofenamate, Mefenamic Acid, Meloxicam, Nabumetone, Naproxen, Oxaprozin, Phenylbutazone, Piroxicam, Sulindac, Tolmetinopiods, Cox-2 inhibitors such as celcoxib, and narcotic pain medications such as Buprenorphine, Butorphanol, Codeine, Hydrocodone, Hydromorphone, Levorphanol, Meperidine, Methadone, Morphine, Nalbuphine, Oxycodone, Oxymorphone, Pentazocine, Propoxyphene, or the central analgesic tramadol.

The preceding list of additional active agents is meant to be exemplary rather than fully inclusive. Additional active agents not included in the above list may be administered in combination with a compound of Formula I. The additional active agent will be dosed according to its approved prescribing information, though in some embodiments the additional active agent will be dosed at less the typically prescribed dose and in some instances less than the minimum approved dose.

The disclosure includes a method of treating bipolar depression and major depressive disorder where an effective amount of the compound is an amount effective to decrease depressive symptoms, wherein a decrease in depressive symptoms is the achievement of a 50% or greater reduction of symptoms identified on a depression symptom rating scale, or a score less than or equal to 7 on the $HRSD_{17}$, or less than or equal to 5 on the $QID-SR_{16}$, or less than or equal to 10 on the MADRS.

The disclosure provides an amount effective to decrease painful symptoms, wherein a decrease in painful symptom is the achievement of a 50% or greater reduction of painful symptoms on a pain rating scale.

While several embodiments of compounds and methods have been described, it is not intended that the disclosure be limited thereto, as it is intended that the disclosure be as broad in scope as the art will allow and that the specification be read likewise. Persons skilled in the art will understand that the compounds and methods specifically described herein are non-limiting exemplary embodiments. Therefore, the above description should not be construed as limiting, but merely as exemplifications of presently disclosed embodiments. Other elements, steps, methods and techniques that are insubstantially different from those described above and/or in the appended claims are also intended to be within the scope of the disclosure.

What is claimed is:

1. A phenyl cyclohexanone compound of Formula I or pharmaceutically acceptable salt thereof:

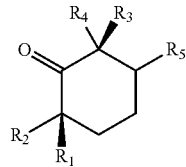

Formula I $R_1$ is —$NH_2$ or —OH;
$R_2$ is,

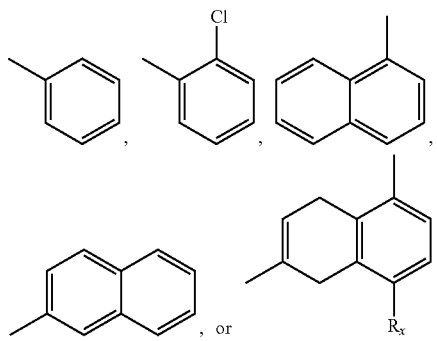

where $R_x$ is Cl, Br, —$OCH_3$, or $NH_2$;
$R_3$ is —OH, —$OCH_3$, —$NH_2$, —CN, —$SO_2$—$NH_2$,

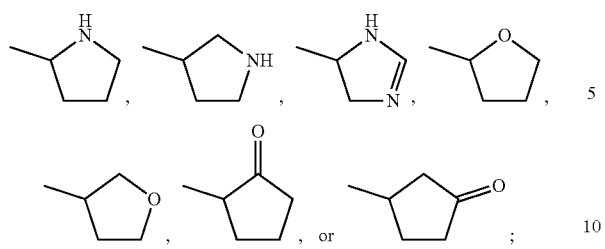
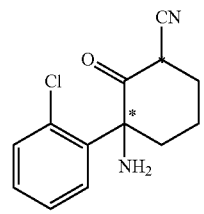
Formula VIII
$R_4$ is —OH, or —OCH$_3$; and
$R_5$ is —OH, —NH$_2$, or =O.
2. A stereoisomer of a compound of claim 1.
3. A phenyl cyclohexanone compound selected from:
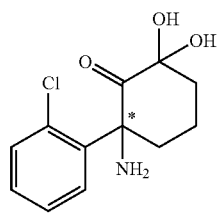
Formula III
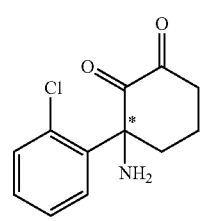
Formula IX
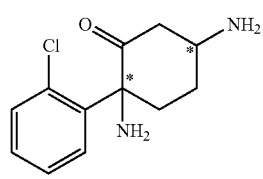
Formula IV
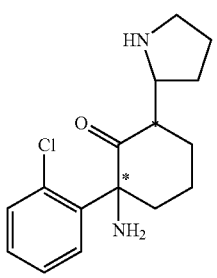
Formula X
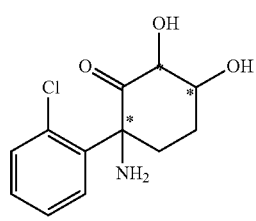
Formula V
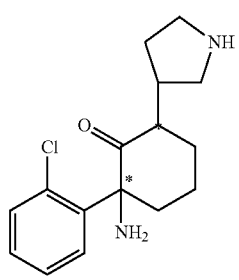
Formula XI
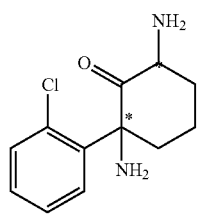
Formula VI
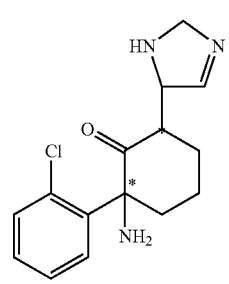
Formula XII
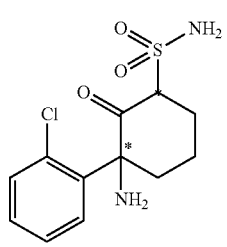
Formula VII
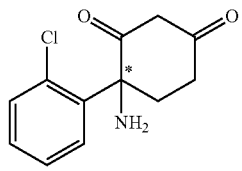
Formula XIII 19
-continued Formula XIV

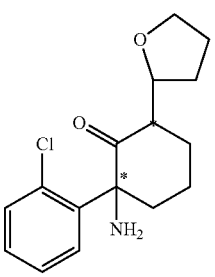

Formula XV

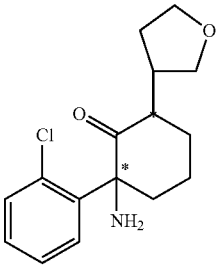

Formula XVI (structure with Cl-phenyl, NH2, cyclohexanone, and cyclopentanone substituent)

4. A phenyl cyclohexanone compound of claim 1 wherein there is a cis stereochemical relationship between the C2 and C6 chiral centers on the cyclohexanone ring.

5. A phenyl cyclohexanone compound of claim 1 wherein the C2 carbon of the cyclohexanone ring is in an S configuration.

6. A pharmaceutical composition comprising a phenyl cyclohexanone compound in accordance with claim 1 and a pharmaceutically acceptable carrier.

7. A method of treatment comprising administering a pharmaceutical composition in accordance with claim 6 to a patient in need of treatment for bipolar depression, major depressive disorder, schizophrenia, Alzheimer's dementia, amyotrophic lateral sclerosis, complex regional pain syndrome (CRPS), chronic pain, or neuropathic pain.

8. A method of inhibiting NMDA receptor activity comprising contacting cells with a concentration of a compound in accordance with claim 1 sufficient to inhibit NMDA receptor activity.

9. A method of modifying endogenous concentrations of D-Serine comprising contacting cells with a concentration of a compound in accordance with claim 1 sufficient to modify endogenous concentrations of D-Serine.

10. A method of stimulating the activating phosphorylation of mTOR comprising contacting cells with a concentration of a compound in accordance with claim 1 sufficient to stimulate the activating phosphorylation of mTOR.

11. A method of inhibiting nAChR activity comprising contacting cells with a concentration of a compound in accordance with claim 1 sufficient to inhibit nAChR activity.

12. A method of inhibiting serine racemase (SR) comprising contacting cells with a concentration of a compound in accordance with claim 1 sufficient to inhibit SR.

20

13. A phenyl cyclohexanone compound or a pharmaceutically acceptable salt of the formula:

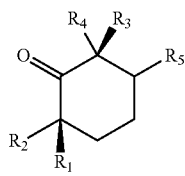

$R_1$ is —$NH_2$ or OH;
$R_2$ is,

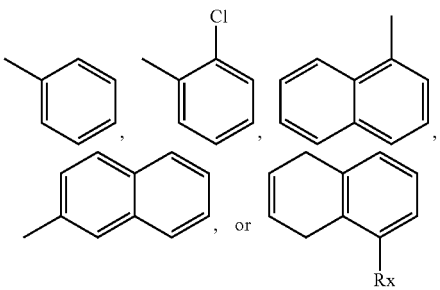

where $R_x$ is Cl, Br, —$OCH_3$, or —$NH_2$;

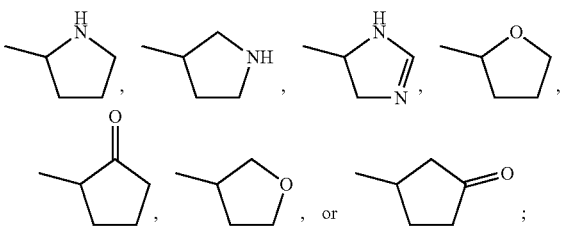

$R_3$ is —OH, —CN, —$SO_2$—$NH_2$
$R_4$ is —H, —OH, or —$OCH_3$, and
$R_5$ is —OH, —$NH_2$, or =O.

14. A pharmaceutical composition comprising a phenyl cyclohexanone compound in accordance with claim 13 and a pharmaceutically acceptable carrier.

15. A method of treatment comprising administering a pharmaceutical composition in accordance with claim 14 to a patient in need of treatment for bipolar depression, major depressive disorder, schizophrenia, Alzheimer's dementia, amyotrophic lateral sclerosis, complex regional pain syndrome (CRPS), chronic pain, or neuropathic pain.

16. A method of inhibiting NMDA receptor activity comprising contacting cells with a concentration of a compound in accordance with claim 14 sufficient to inhibit NMDA receptor activity.

17. A method of modifying endogenous concentrations of D-Serine comprising contacting cells with a concentration of a compound in accordance with claim 14 sufficient to modify endogenous concentrations of D-Serine.

18. A method of stimulating the activating phosphorylation of mTOR comprising contacting cells with a concentration of a compound in accordance with claim 14 sufficient to stimulate the activating phosphorylation of mTOR.

19. A method of inhibiting nAChR activity comprising contacting cells with a concentration of a compound in accordance with claim 14 sufficient to inhibit nAChR activity.

20. A method of inhibiting serine racemase (SR) comprising contacting cells with a concentration of a compound in accordance with claim 14 sufficient to inhibit SR.

\* \* \* \* \*